United States Patent
Adams et al.

(10) Patent No.: US 7,713,258 B2
(45) Date of Patent: May 11, 2010

(54) DISPOSABLE INFUSION DEVICE FACILITATING TISSUE FOLD FORMATION FOR CANNULA DEPLOYMENT AND METHOD

(75) Inventors: John M. Adams, Kirkland, WA (US); Clifton A. Alferness, Port Orchard, WA (US)

(73) Assignee: Calibra Medical, Inc., Redwood City, CA (US)

( * ) Notice: Subject to any disclaimer, the term of this patent is extended or adjusted under 35 U.S.C. 154(b) by 0 days.

(21) Appl. No.: 12/205,655

(22) Filed: Sep. 5, 2008

(65) Prior Publication Data

US 2009/0048578 A1    Feb. 19, 2009

Related U.S. Application Data

(62) Division of application No. 11/651,425, filed on Jan. 9, 2007.

(51) Int. Cl.
*A61M 31/00* (2006.01)
(52) U.S. Cl. .................. 604/513; 604/506; 604/174; 604/180
(58) Field of Classification Search ........... 604/500, 604/502, 506, 513, 174, 177, 180, 164.01, 604/164.04, 167.01, 167.02, 288.01, 288.02
See application file for complete search history.

(56) References Cited

U.S. PATENT DOCUMENTS

| | | | |
|---|---|---|---|
| 5,685,859 A | 11/1997 | Kornerup | |
| 6,702,779 B2 | 3/2004 | Connelly et al. | |
| 7,070,580 B2 | 7/2006 | Nielsen | |
| 7,303,543 B1 * | 12/2007 | Maule et al. | 604/93.01 |
| 2005/0107743 A1 | 5/2005 | Fangrow | |
| 2008/0021375 A1 * | 1/2008 | Burns et al. | 604/27 |

OTHER PUBLICATIONS

Kim, Jung Tae, PCT International Search Report, May 20, 2008.

* cited by examiner

*Primary Examiner*—Nicholas D Lucchesi
*Assistant Examiner*—Bhisma Mehta
(74) *Attorney, Agent, or Firm*—Richard O. Gray, Jr.; Graybeal Jackson LLP

(57) ABSTRACT

A device and method facilitates the forming of a skin fold during deployment of a cannula. The device may be a disposable infusion device and the method comprises adhering, to a skin surface, a base member having a port for receiving a cannula, forming a skin fold having skin surfaces sloping away from opposite sides of the base member, driving a cannula through the port of the base member while maintaining the skin fold, and releasing the skin fold. To facilitate the forming of the skin fold, the device comprises a base having a base surface and a flexible layer member. The flexible layer member has a first surface adjacent the base surface and a second surface adapted to be adhered to a patient's skin. The first surface has a first portion adhered to a portion of the base surface and a second portion adherable to the base surface.

6 Claims, 3 Drawing Sheets

DISPOSABLE INFUSION DEVICE FACILITATING TISSUE FOLD FORMATION FOR CANNULA DEPLOYMENT AND METHOD

PRIORITY CLAIM

The present application is a divisional of co-pending U.S. patent application Ser. No. 11/651,425, fired Jan. 9, 2007, which is incorporated herein by reference in its entirety

BACKGROUND OF THE INVENTION

Tight control over the delivery of insulin in both type I diabetes (usually juvenile onset) and type II diabetes (usually late adult onset), has been shown to improve the quality of life as well as the general health of these patients. Insulin delivery has been dominated by subcutaneous injections of both long acting insulin to cover the basal needs of the patient and by short acting insulin to compensate for meals and snacks. Recently, the development of electronic, external insulin infusion pumps has allowed the continuous infusion of fast acting insulin for the maintenance of the basal needs as well as the compensatory doses (boluses) for meals and snacks. These infusion systems have shown to improve control of blood glucose levels. However, they suffer the drawbacks of size, cost, and complexity. For example, these pumps are electronically controlled and must be programmed to supply the desired amounts of basal and bolus insulin. This prevents many patients from accepting this technology over the standard subcutaneous injections.

Hence, there is a need in the art for a convenient form of insulin treatment which does not require significant programming or technical skills to implement to service both basal and bolus needs. Preferably, such a treatment would be carried out by an infusion device that is simple to use and mechanically driven negating the need for batteries and the like. It would also be preferable if the infusion device could be directly attached to the body and not require any electronics to program the delivery rates. The insulin is preferably delivered through a small, thin-walled tubing (cannula) through the skin into the subcutaneous tissue similar to technologies in the prior art.

While the idea of such a simple insulin delivery device is compelling, many obstacles must be overcome before such a device may become a practical realty. One problem resides in insulin supply. Patients vary greatly on the amount of insulin such a device must carry to provide treatment over a fixed time period of, for example, three days. This is one environment where one size does not fit all.

Another problem is with cannula deployment to support insulin delivery. Cannula deployment to support delivery of the insulin beneath the patient's skin must be made easy and convenient. This is not as easy as it seems because cannula deployment, as generally and currently performed in the art, requires insertion of a cannula-carrying needle into the patient and then retraction of only the needle to leave the cannula in place beneath the patient's skin.

When needles are introduced beneath a patient's skin, during an injection, for example, it is well known that the pain associated with the injection may be reduced by forming a fold in the skin at the injection site prior to the injection. The fold of skin can also increase the probability that only soft tissue will be affected during the injection. However, the forming of such a skin fold when the needle is also being driven through an associated device, such as in infusion device, for example, to deliver a cannula to a deployed position extending from the device to beneath the skin is not readily possible. The reason for this is that in such cases, the device is already adhered to the skin and covers the injection site, making it virtually impossible to form a desired skin fold to receive the needle and cannula. As will be seen subsequently, the present invention addresses these and other issues toward providing a simple, practical, reliable and relatively pain-free deployment of a cannula beneath the skin to support insulin delivery.

SUMMARY OF THE INVENTION

The invention provides a medical device comprising a base having a base surface and a flexible layer member. The flexible layer member has a first surface adjacent the base surface and a second surface adapted to be adhered to a patient's skin. The first surface has a first portion adhered to a portion of the base surface and a second portion adherable to the base surface.

The base surface and the flexible layer member may be arranged to permit a cannula to pass there through from the base. The base may be arranged to permit a cannula to pass through the first portion of the first surface. The base may include a septum within the base surface to permit a cannula to pass through the first portion of the first surface.

The second portion of the first surface may include a layer of adhesive and a removable cover overlying the layer of adhesive. The second portion of the first surface may include first and second areas on opposite sides of the first portion. The base surface and the flexible layer member are preferably arranged to permit a cannula to pass there through from the base. The base may be further arranged to permit a cannula to pass through the first portion of the first surface. The base may include a septum within the base surface to permit a cannula to pass there the first portion of the first surface. The first and second areas of the first surface may each include a layer of adhesive and a removable cover overlying the layer of adhesive.

The invention may further provide a method of deploying a cannula of a disposable infusion device. The method comprises the steps of adhering, to a skin surface, a base member having a port for receiving a cannula, forming a skin fold having skin surfaces sloping away from opposite sides of the base member and driving a cannula through the port of the base member while maintaining the skin fold and thereafter releasing the skin fold.

The step of forming the skin fold may include compressing soft tissue beneath and on opposite sides of the base member. The adhering step may include adhering a first portion of the base member to the flexible member before forming the skin fold and adhering an additional portion of the base member to the flexible member after releasing the skin fold. The additional portion of the base member may be a portion of the base member remaining to be adhered to the flexible member.

The method may further include the step of releasably attaching to the base member a cannula driver having a cannula and a drive mechanism for driving the cannula from the cannula driver into and through the port of the base member. The driving step may then include actuating the drive mechanism to drive the cannula into and through the base member port.

The method may include the further step of removing the cannula driver from the base member after the cannula has been driven through the base member port to a deployed position extending from the base member to beneath the skin. The step of forming the skin fold may include compressing soft tissue beneath and on opposite sides of the base member.

The adhering step may include the steps of adhering a first portion of the base member to the flexible member before forming the skin fold and adhering an additional portion of the base member to the flexible member after releasing the skin fold. The additional portion of the base member may be a portion of the base member remaining to be adhered to the flexible member.

BRIEF DESCRIPTION OF THE DRAWINGS

The features of the present invention which are believed to be novel are set forth with particularity in the appended claims. The inventions together with further features and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
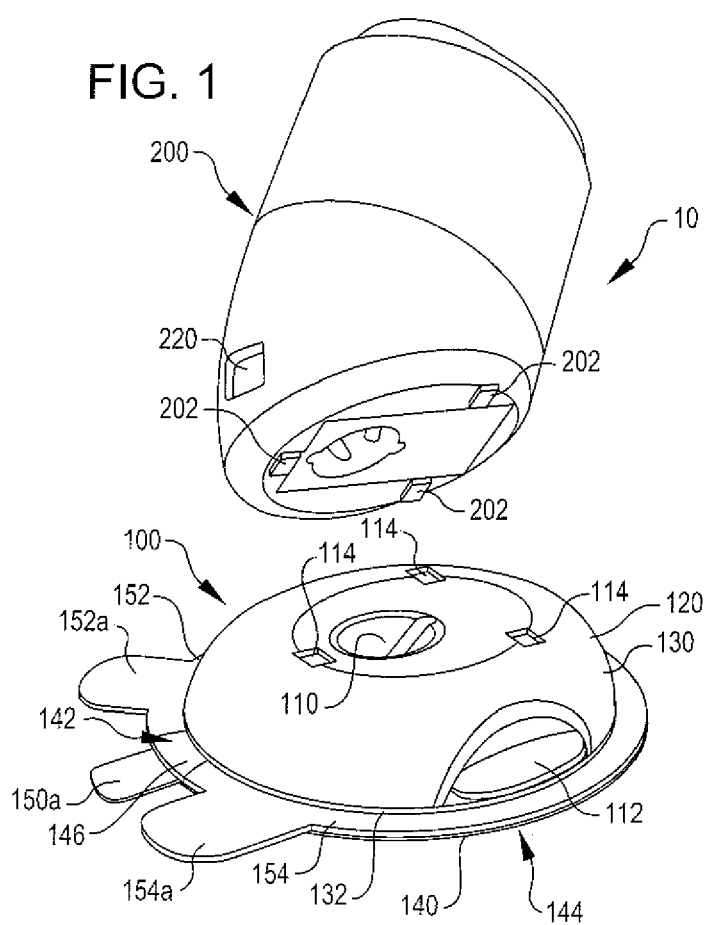
FIG. 1 is a perspective view of a disposable infusion device according to an embodiment of the invention together with a cannula driver that provides the infusion device with a cannula for the delivery of a liquid medicant.

Referring now to FIG. 1, it is a perspective view of an infusion system 10 according to an embodiment of the present invention. The infusion system 10 generally includes an infusion device 100 and a cannula driver 200. The device 100 includes a septum 110 for both receiving a cannula to be deployed and receiving boluses of insulin with a needle syringe, fox example. The device 100 further includes a body 120 having a base 130 and a flexible member 140.

The base 130 has a base surface 132 and the flexible member 140 includes a first surface 142 adjacent the base surface 132 of the device base 130 and a second surface 144 adapted to be adhered to the skin. The flexible member 140 carries three protective strips 150, 152, and 154. Each strip has a respective tab 150a, 152a, and 154a to facilitate its removal. The first strip 150, when removed, exposes a layer of adhesive for use in adhering the second surface 144 of the flexible member 140 to the patient's skin. The second and third strips 152 and 154, when removed, expose an adhesive on the first surface 142 of the flexible member to the base surface 132 of the device. The strips 152 and 154 cover outer regions of the flexible member first surface 142 leaving a center region 146 already adhered to the base surface 132 of the device base 130. As will be seen subsequently, after a cannula has been deployed, the strips 152 and 154 may be removed to expose the adhesive in the outer regions of the first surface 142 of the flexible member 140 to the base surface 132 of the device 130. This permits the entire base surface 132 to be adhered to the flexible member 140 to more fully stabilize the device 100 on the patient's skin after cannula deployment.

The device 100 further includes a pair of actuator buttons of which one such button 112 may be seen in FIG. 1. The device 100 is preferably arranged so that only concurrent depression of the actuator buttons results in insulin being dispensed to the patient.

The cannula driver 200 is arranged to be detachably received on the infusion device 100 to facilitate deployment of a cannula from the device 100. To that end, the driver 200 includes a plurality of projections 202 that are arranged to align with and be frictionally received by a like plurality of recesses 114 within the body 120 of the infusion device 100. The projections 202 and the recesses 114 are correspondingly arranged to serve the further function of aligning the cannula driver 200 with the infusion device 100 for cannula deployment. The cannula driver 200 still further includes an actuator button 220. When the actuator button 220 is depressed, a mechanism (not shown) within the cannula driver is released to first drive a cannula carried on a cannula needle through the device 100 to a deployed position and then retract the needle back into the cannula driver 200 leaving the cannula deployed and ready to provide insulin to the patient. For a complete description of an exemplary cannula driver, reference may be had to copending application Ser. No. 11/641,596, filed Dec. 18, 2006 for CANNULA DELIVERY APPARATUS AND METHOD FOR A DISPOSABLE INFUSION DEVICE, which application is assigned to the assignee of the present invention and incorporated in its entirety herein by reference.

Figure 2:
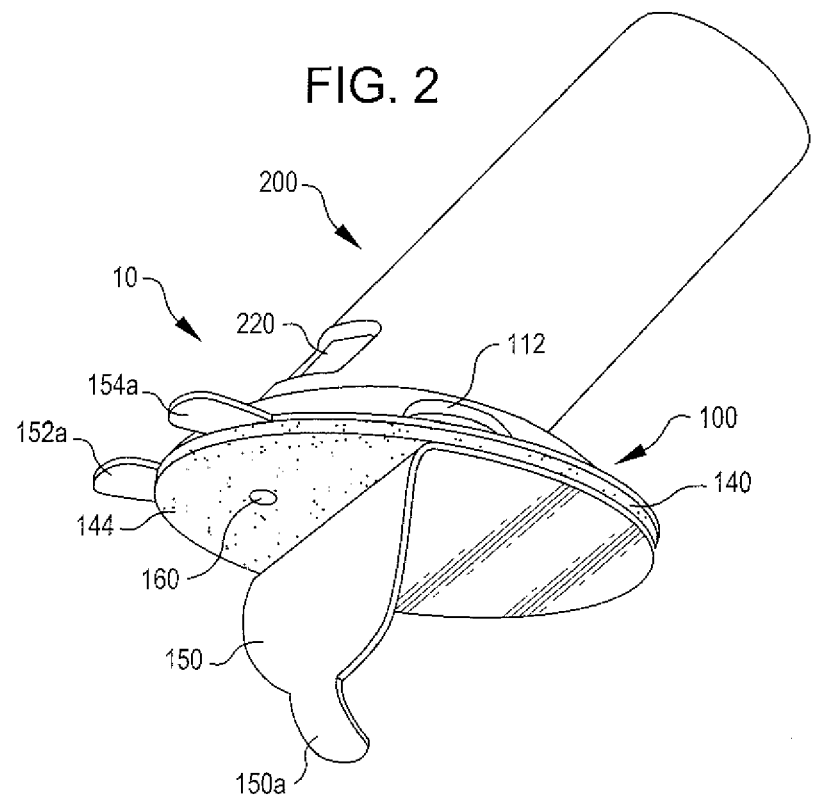
FIG. 2 is perspective view of the cannula driver of FIG. 1 detachably received by the infusion device of FIG. 1 before the device is adhered to the skin.

FIGS. 2-7 illustrate a manner in which the infusion device 100 may be deployed on a patient's skin according to an embodiment of the present invention for providing a liquid medicant, such as insulin, to the patient. In FIG. 2, it may be seen that the cannula driver 200 has been detachably received by the infusion device 100. The strip 150 is partly removed, as by the pulling of the tab 150a, to expose the adhesive coated second surface 144 of the flexible member 140 to be adhered to the patient's skin. Also exposed in this process is a port 160 that communicates with the septum 110 of the infusion device 100. The port 160 permits the cannula to be deployed to pass through the base 130 of the device 100 and the flexible member 140 into its deployed position as will be seen subsequently. It is noted that the port is located equidistant and in between the tabs 152a and 154a so that the cannula passes through the central region 146 (FIG. 1) of the first surface 142 of the flexible member 140 already adhered to the device 100.

Figure 3:
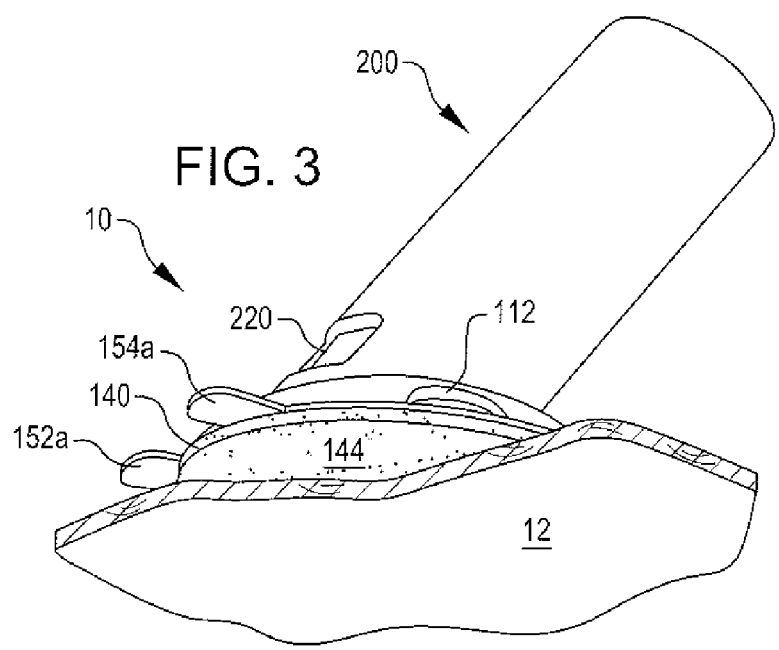
FIG. 3 is a perspective view of the infusion device and cannula driver of FIG. 1 after the device is adhered to the skin.

FIG. 3 shows the infusion system 10 after the strip 150 is removed and the second surface 144 of the flexible member 140 is adhered to the patient's skin 12. It may be noted that the tabs 152a and 154a are still in place and that their corresponding strips have not yet been removed.

Figure 4:
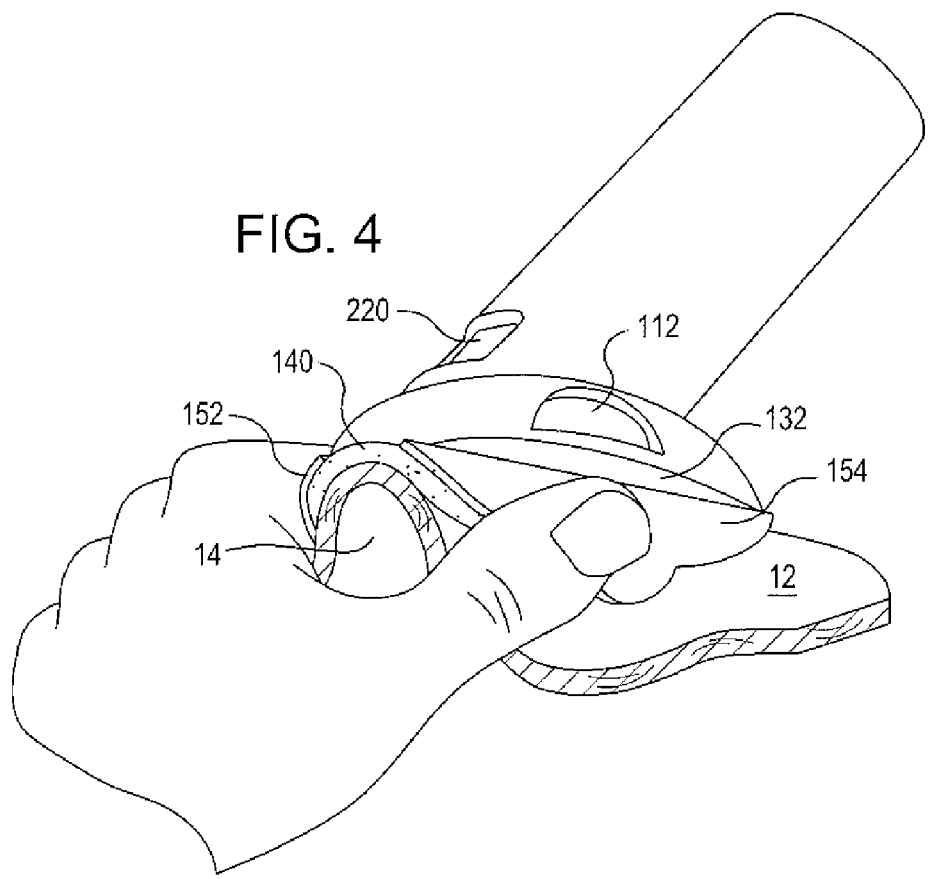
FIG. 4 is a perspective view of the infusion device and cannula driver of FIG. 1 after the device is adhered to the skin and as a skin fold is formed to receive a cannula from the cannula driver.

FIG. 4 shows a next step in the deployment process. Since the strips 152 and 154 have not yet been removed, the outer regions of the first surface of the flexible member 140 are not adhered to the base surface 132 of the device 100. Thus, the outer regions of the flexible member 140 remain flexible to facilitate the formation of a skin fold 14 of soft tissue on opposite sides of the device 100. More particularly, and as may be seen in FIG. 4, the fold of soft tissue is formed by the compression of soft tissue on opposite sides of the central region of the base surface 132 so that the surface of the skin 12 slopes away from opposite sides of the central region of the base surface 132. The patient is now ready to actuate the cannula driver 200.

Figure 5:
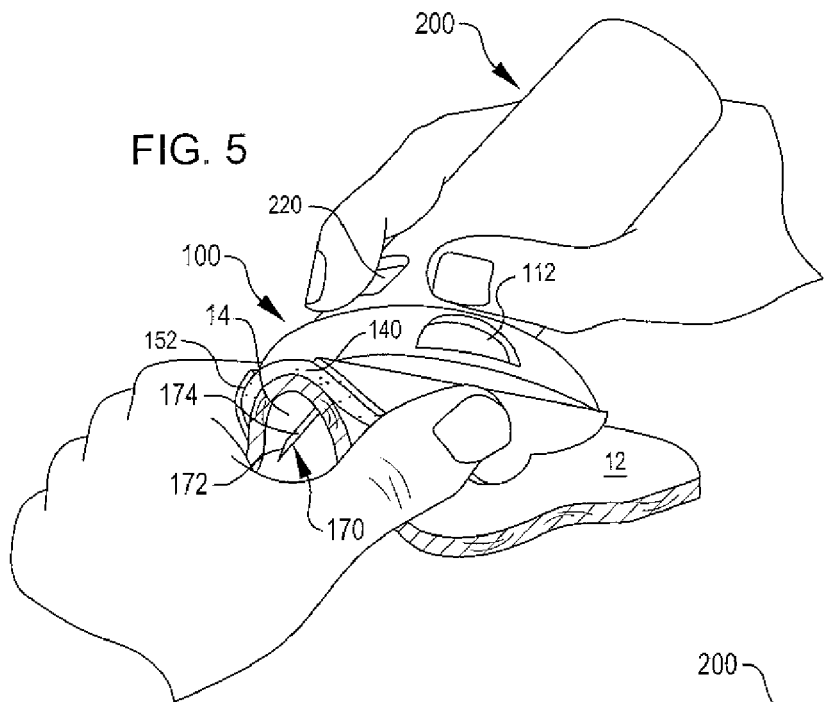
FIG. 5 is a perspective view of the infusion device and cannula driver of FIG. 1 as a needle and cannula are driven into the skin fold according to an embodiment of the invention.

FIG. 5 shows the cannula driver 200 being actuated. Here it may be seen as the skin fold 14 is maintained with one hand, the actuator button 220 is depressed with the other hand. This causes a cannula/needle assembly 170 to be driven from the cannula driver 200 and through the device 100 to cause the assembly 170 to project from the device 100 to beneath the patient's skin 12. By virtue of the formed skin fold 14, the pain associated with the assembly driving is reduced and the probability of affecting only soft tissue is greatly enhanced.

The assembly 170 is seen with the cannula 174 being carried by a needle 172. Once the assembly is positioned as shown, the needle 172 is withdrawn from the cannula 174 and preferably transported back to the cannula driver 200 for safe sharps disposal.

Figure 6:
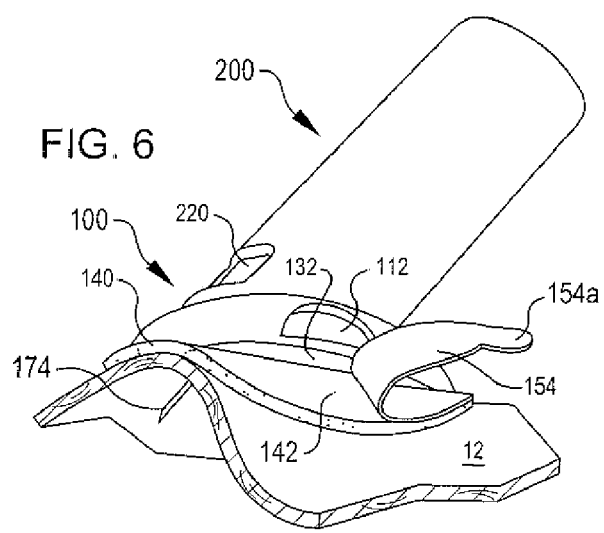
FIG. 6 is a perspective view of the infusion device and cannula driver of FIG. 1 after the needle has been retracted from the cannula back into the cannula driver and as an adhesive is exposed to the device to more completely secure the device with respect to the skin in accordance with an embodiment of the invention.

With the cannula 174 deployed and the needle 172 withdrawn back into the cannula driver 200 as shown in FIG. 6, the strips 152 and 154 may now be removed FIG. 6 shows strip 154 being removed by the pulling on its corresponding tab 154a. The strip 152 may be removed in the same manner. This exposes the adhesive on the outer regions of the flexible member first surface 142 to the base surface 132. The outer regions of the first surface 142 of the flexible member 140 may now be brought into engagement with the base surface 132 of the infusion device 100 to more completely stabilize the device 100 on the patient's skin 12. The cannula driver 200 may now be separated from the infusion device 100. The infusion device 100 will now be fully deployed as shown in FIG. 7.

Figure 7:
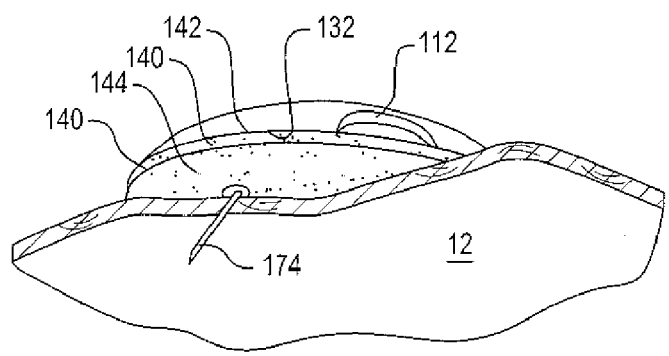
FIG. 7 is a perspective view of the infusion device of FIG. 1 after the cannula driver has been removed from the infusion device and the cannula has been fully deployed to facilitate the delivery of insulin through the cannula to beneath the skin.

In FIG. 7, it may be seen that the second surface 144 of the flexible member 140 is solidly adhered to the skin 12. The first surface 142 of the flexible member 140 is solidly adhered to the base surface 132 of the infusion device 100. The device 100 is fully stabilized on the patient's skin 12. The cannula extends from the device 100 beneath the skin 12 in a fully deployed position. Depression of the actuator buttons 112 will now cause insulin to be provided to the patient through the deployed cannula 174.

While particular embodiments of the present invention have been shown and described, modifications may be made, and it is therefore intended in the appended claims to cover all such changes and modifications which fall within the true spirit and scope of the invention as defined by those claims.

What is claimed:

1. A method of deploying a cannula of a disposable infusion device, comprising:
   providing a device comprising a base member and a flexible member partially adhered to the base member, wherein the flexible member comprises first and second surfaces, the first surface comprising an outer region;
   adhering the second surface to a skin surface;
   forming a skin fold;
   driving a cannula through the base member while maintaining the skin fold;
   releasing the skin fold; and
   adhering the outer region of the first surface to the base member.

2. The method of claim 1, wherein the step of forming the skin fold includes compressing soft tissue beneath and on opposite sides of the base member.

3. The method of claim 1, including the further step of removing the cannula driver from the base member after the cannula has been driven through the base member to a deployed position extending from the base member to beneath the skin.

4. The method of claim 3, wherein the step of forming the skin fold includes compressing soft tissue beneath and on opposite sides of the base member.

5. The method of claim 4, wherein the adhering step includes adhering a first portion of the base member to the flexible member before forming the skin fold and adhering an additional portion of the base member to the flexible member after releasing the skin fold.

6. The method of claim 5, wherein the additional portion of the base member is a portion of the base member remaining to be adhered to the flexible member.

* * * * *